United States Patent [19]

Tusim

[11] 4,376,799
[45] Mar. 15, 1983

[54] QUIET FILM AND CONTAINER
[75] Inventor: Martin H. Tusim, Fresno, Calif.
[73] Assignee: The Dow Chemical Company, Midland, Mich.
[21] Appl. No.: 187,660
[22] Filed: Sep. 16, 1980
[51] Int. Cl.³ .................. B32B 7/02; B32B 27/08; A61F 5/44
[52] U.S. Cl. .................. 428/213; 428/283; 428/215; 428/216; 428/515; 428/518
[58] Field of Search ............... 428/216, 518, 515, 349; 128/283; 525/192, 240, 227

[56] References Cited

U.S. PATENT DOCUMENTS 3,086,957 4/1963 Carter ................................ 525/192
3,302,647 2/1967 Marsan ............................... 128/283
3,355,519 11/1967 Muller et al. ....................... 525/240
3,524,795 8/1970 Peterson ............................. 428/216

*Primary Examiner*—Thomas J. Herbert, Jr.
*Attorney, Agent, or Firm*—Lloyd E. Hessenaur, Jr.

[57] ABSTRACT

A substantially rustle-free thermoplastic film and container made therefrom. The film may be a multilayer structure, a skin of which is formed of a chlorinated polyethylene resin blend. The composition of said structure is such that quietness is imparted without detracting from the extrudability and other physical characteristics necessary for practical applications. A vapor barrier may be included as a core layer. A particular application for the present invention is an ostomy bag.

11 Claims, 4 Drawing Figures

QUIET FILM AND CONTAINER

BACKGROUND OF THE INVENTION

This invention relates primarily to pouches, bags and other containers where there is a need to have minimal noise from the container in its use. This is particularly desirable in items such as surgical drainage pouches, sometimes known as ostomy bags, which permit drainage from parts of the body and are temporarily worn by a patient such as that illustrated in U.S. Pat. No. 3,302,647, for example. The container should have minimal or no bag rustle when worn because the resulting noise can often be embarrassing or disturbing to the wearer. Also, without such noise, it is easier for the wearer to remove from his mind the fact that he is required to wear such a product. Prior containers have been unable to provide adequate odor and moisture barrier properties while at the same time achieving a desirable structural thinness and a high degree of quietness.

Present films for containers of this nature generally are made from simple polyethylene films or from more expensive plasticized polyvinyl chloride film, plasticized polyvinylidene chloride copolymer films and multilayered structures such as ethylene vinyl acetate/polyvinylidene chloride/ethylene vinyl acetate combination films. To a greater or lesser extent, the more desirable thin gauge containers having a high degree of odor and moisture barrier have a noise level such that they rustle when worn by the user. There is a need for a substantially rustle-free product which is economical to make, has good odor and moisture barrier properties, and is sufficiently sturdy for its intended purposes.

SUMMARY OF THE INVENTION

The purpose of the present invention is to obtain a practical thermoplastic film container, particularly one useable in medial applications, which has physical properties which provide a high degree of quietness. Such a product shall also have sufficient softness and comfort, heat sealability, toughness and, where desirable or necessary, adequate moisture and gas or odor barrier. It has been discovered that a thermoplastic container having all of the above desirable properties can be obtained by use of a multilayered thermoplastic film having chlorinated polyethylene blend skins with a core of a barrier thermoplastic resin such as polyvinylidene chloride or Saran resin. The film must possess a degree of quietness which is near rustle-free and insignificant to the background noise to accomplish the improvements desired. For skin compositions and multilayer arrangement of the film for the present container combine to accomplish the desired results of this invention, including particular preferred embodiments thereof. The degree of quietness is measured by a testing method developed for this invention.

DETAILED DESCRIPTION OF THE INVENTION

Figure 1:
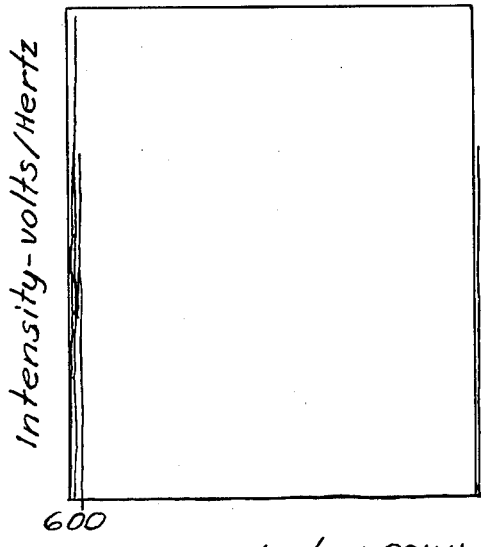
FIG. 1 is an approximate graphical representation of the intensity and frequency levels of background noise against which the noise levels of prior art and other products, and the products of this invention were measured.

The invention comprehends a modification of a current ostomy bag film, such as typified in U.S. Pat. No. 3,524,795. In this particular prior art structure, polyethylene skins are formed about a Saran (polyvinylidene chloride copolymer) resin core with certain glue layers in between to adhere the skins to the core. Such a film exhibits a noise level which if reduced 15 percent or 20 percent would make the film practically rustle-free and thus very attractive to the user. It was discovered that by introducing a blend of resins, the major component of which is chlorinated polyethylene, with a typical low-density polyethylene together with a certain small percentage of other additives, that the desired quiet film could be achieved. It was additionally discovered that not only was quietness assured, but the glue layers between the skins and the core which, while permissible for some applications, would not be usually required because of the naturally adhesive character of the chlorinated polyethylene resin. One preferred embodiment of the invention involves a chlorinated polyethylene resin such as that disclosed in an article entitled, "Structure-Property Relationships of Chlorinated Polyethylene", by N. K. Kalfoglou and H. L. williams in *Polymer Engineering and Science,* May, 1972, Volume 12, No. 3, starting at page 224 and in U.S. Pat. Nos. 3,396,901, 3,454,544 and 3,678,873, the teachings of all of which are fully incorporated herein by reference.

More specifically, the chlorinated olefin polymers found to be useful for the purposes of the present invention are preferably prepared by the chlorination, in suspension in an inert diluent, of polyethylene or interpolymers containing at least about 90 mole percent of ethylene in the polymer molecule with any remainder being one or more ethylenically unsaturated comonomers wherein such polymers are preferably of an essentially linear structure. Chlorinated olefin polymers contain from about 25 to 50, and preferably about 36 weight percent of chemically combined chlorine and are characterized by having a relative crystallinity of between about 15 and 28 percent when containing about 25 weight percent chlorine and a relative crystallinity of less than about 10 percent when containing about 34 or more weight percent chlorine, wherein said relative crystallinity is a measure of the ratio of the crystalline peak areas to the sum of the amorphous plus crystalline peak area as determined by conventional X-ray diffraction techniques.

Exemplary of preferred polyolefin materials to be chlorinated are those distinct species and varieties of essentially linear and unbranched highly porous, finely divided polymers containing at least about 90 mole percent ethylene in the polymer molecule with the remainder being one or more ethylenically unsaturated comonomers such as the nonaromatic hydrocarbon olefins having 3 or more carbon atoms, including propylene, butene-1 and butene-2 and 1,7-octadiene and the like; cycloaliphatic olefins such as 1,5-cyclopentene and cyclooctadiene and the like, substituted olefins such as acrylic acid and its esters; conjugated diolefins such as butadiene and the like; and the alkenyl aromatic compounds such as styrene and its derivatives, among many other polymerizable materials know to the art.

The ethylenic polymer resins used in the present invention can include low or medium density polyethylene or ethylene copolymers which comprise ethylene in at least one monoethylenically unsaturated comonomer, especially another lower olefin or a carboxylic acid or an alkyl ester of a monoethylenically unsaturated carboxylic acid. Examples of such copolymers include ethylene-propylene copolymer, ethylene acrylic acid, ethylene methyl methacrylate copolymer, ethylene vinyl acetate copolymer, and the like. Blends of one or more of the ethylenic polymer resins may also be used. Methods of making ethylenic polymer resins described hereinabove are readily known in the art.

The term "low-density polyethylene" as used herein means branched polyethylene having a density from about 0.910 to about 0.930 g/cc and a melt index from about 0.1 to about 10 dg.min. "Medium-density polyethylene" may have a density from about 0.931 to about 0.940.

A preferred chlorinated polyethylene resin comprises 36 percent chlorine resin having a melt index around 2 and a density of about 1.16 with a crystallinity of less than about 2 percent. Resins with a higher or lower chlorine level may also be beneficial. For example, a chlorine content range of 30 to 42 percent may result in an improved overall processability of the blend and in improved properties of the resulting film. The quietness exhibited by the chlorinated polyethylene blend may be related to its rubbery or elastic nature.

A preferred embodiment of a skin formulation for the film of this invention can be, for example, one having about 70 to 80 percent by weight of chlorinated polyethylene, such as identified above, about 17 to 27 percent by weight of a low-density polyethylene, such as The Dow Chemical Company's PE-535, and stabilizers such as about 1 or 2 percent by weight of a calcium stearate and 1 percent by weight of Paraplex G60 or G62 commercial stabilizers, the stabilizers helping to prevent thermal degradation of the chlorinated polyethylene at extrusion temperatures. The barrier resin core can be a vinylidene chloride-vinyl chloride copolymer, ethylene divinyl alcohol, a resin by Monsanto Chemical Company called "Verex resin" and other barrier resins such as that identified in U.S. Pat. No. 3,549,389, for example, to produce a film which has excellent gas and water vapor barrier properties. The overall thickness of the film for pouches or other containers can be about 2.8 mils, each of the skins being about 1.3 mils in thickness and the barrier resin core being about 0.25 mil in thickness. The thicknesses of the various film layers can vary depending on the degree of toughness and barrier required for each application. For example, the entire film guage thickness can range from about 2.0 mils to about 5.0 mils with corresponding proportional changes in the skin and core layers as may be practical and desirable for an ostomy pouch application. The multilayer film used in this invention can be made by coextrusion such as typified by U.S. Pat. Nos. 3,354,506, 3,557,265 and 3,625,348.

The chlorinated polyethylene blend formulation described above has been developed to balance film properties and extrudability of the resin blend. The more chlorinated polyethylene resin in the blend, the quieter the film but the more difficult it is to extrude. The higher the chlorine content in the resin blend, the more likely the resin blend may thermally degrade at extrusion temperatures. Other properties also depend on the percent of chlorinated polyethylene in the blend. The degree of softness and comfort is increased with the percentage of chlorinated polyethylene resin in the blend because the resin has a relatively low modulus when compared to other film resins. Further, as the chlorine level of the chlorinated polyethylene is increased, the modulus can be lowered to increase quietness and comfort. The chlorinated polyethylene blend films of this invention are also tough even though tensile strength properties are not as high as in other films. The percentage of chlorinated polyethylene in the blend can also affect sealability as the chlorinated polyethylene film has a somewhat lower heat seal strength than that of polyethylene generally. However, the higher percentage of chlorinated polyethylene can advantageously affect the radio frequency sealing because of its dielectric nature. The percentage of chlorinated polyethylene in the film blend does not significantly affect oxygen and vapor barrier properties since that is basically controlled by the barrier core layer. The addition to the blend of low-density polyethylene can include alternately or in addition linear low-density polyethylene, i.e., low-density polyethylene made by a low-pressure process, ethylene vinyl acetate, ethylene acrylic acid and other well-known olefinic polymers and copolymers. Generally, blends containing from about 40 percent to about 95 percent chlorinated polyethylene provide satisfactory results.

It generally is desirable to maintain as simple a structure as possible. A three-layer chlorinated polyethylene blend skin/Saran resin core/chlorinated polyethylene blend skin combination is contemplated as a preferred embodiment of this invention. There is ordinarily enough natural adhesion between the skins and the core layer such that intermediate glue layers are not required. However, there may be particular instances for a film having more than three layers. For example, a five-layer film comprising chlorinated polyethylene blend skin/chlorinated polyethylene blend intermediate layer/Saran resin core/chlorinated polyethylene blend intermediate layer/chlorinated polyethylene blend skin can be formed in which the two intermediate layers of chlorinated polyethylene blend are extruded at lower temperatures than the outer skin layers of chlorinated polyethylene blend to improve the output rate as well as perhaps the haze condition of the film. A hotter polymer on the skin layer gives smooth surfaces to achieve the improved haze condition and processability. The cooler intermediate layer protects a heat sensitive core layer. Intermediate layers between the skin and core layers can also be glue layers, such as an ethylene-vinyl acetate copolymer resin, where the same are required with certain materials.

In order to determine the quietness of the film of the present invention with that of the prior art, and other films used in ostomy pouches and similar containers, an apparatus was constructed to flex plastic films in a controlled, repeatable manner. This apparatus utilized an 8.5 by 8.5 centimeter sample that is fastened to a holder in such a manner that the film sample forms a cylinder. The holder is fashioned such that one end of the film sample is held fixed while the other end is allowed to be rotated about the axis of the holder. Noise is generated when a wheel drive is put into contact with the rotating end of the sample holder and causes it to rotate 15.3° in one direction and 15.3° in the other direction. The frequency of this movement is taken at 1 cycle per second.

Figure 2:
FIGS. 2 and 3 are approximate graphical representations of the intensity and frequency levels of prior art and other products, respectively.
Figure 3:
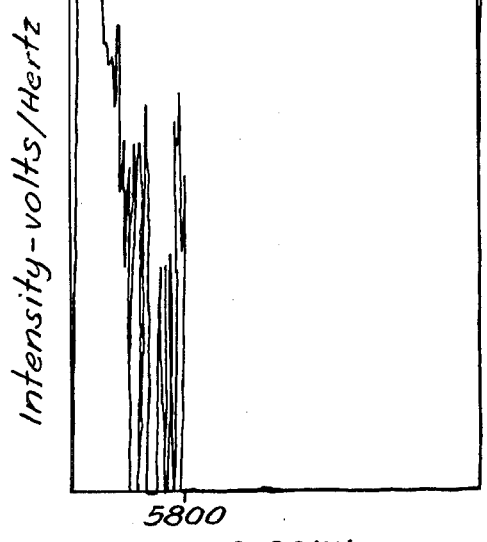

A microphone is used to pick up the noise and the generated noise is analyzed to determine the frequency in a Harmonic Spectrum analyzer. The sound created by the samples in the above manner was measured by placing the microphone in the fixed end of the sample holder creating an electrical signal that may be processed or recorded as desired, as typified in FIGS. 2 to 4 of the drawing. To determine decibel readings the microphone of the spectrum analyzer was replaced with a microphone of an audiometer to pick up the decibel readings. By this technique a direct reading of the sound level over the entire hearing range is available as a single figure expressed in dBA, dBB, or dBC. The unit dBA was selected to report results as it is an accepted decibel noise unit used by most authorities.

Tests were run of film samples having various quantities of chlorinated polyethylene ("CPE") resin blended with either low density polyethylene ("LDPE") or linear low density polyethylene ("LLDPE") comparing the noise levels (or degree of quietness) against background room noise and the noise generated by some of the films currently commercially available, including the most quiet, and other films. The above-described testing apparatus was employed in conducting the tests. It was initially thought that a comparison of decibel (dBA) readings would define the apparent and perceived improvement in quietness achieved by the present invention over that of the prior art. Surprisingly, this did not occur in every instance. Because of this, the frequency value of the various film samples was also checked. This did consistantly confirm the apparent and perceived quietness improvement achieved by the present invention. The following Table summarizes the general results of the findings of the tests.

dBA reading, such as Samples D-1 through F-2 as compared with Prior Art Sample I and Samples C-1 and C-2 of this group. This perceived difference registers in the frequency readings where Samples D-1 through F-2 all show frequency readings of less than 4000 Hertz while the remainder show frequency readings considerably in excess of 4000 Hertz. These frequency readings are all relative to the background noise level of about 600 Hertz.

Figure 4:
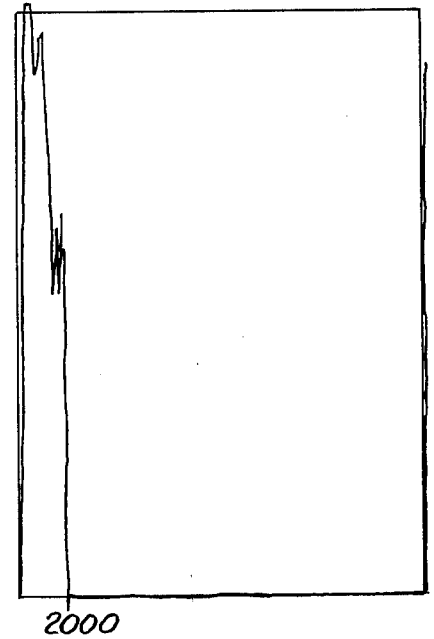
FIG. 4 is an approximate graphical representation of the intensity and frequency level of a typical product made in accordance with the principles of this invention.

To more clearly understand the meaning and significance of the improvements of this invention, reference can be made to the Drawing. FIG. 1 illustrates graphically by the jagged line in the chart the intensity and frequency of the background noise found in the room where the testing occurred. The frequency level of the background noise in this instance was about 600 Hertz. When typical prior film and other film samples were tested, Samples I and C-1, graphically illustrated in FIGS. 2 and 3, respectively, demonstrated a frequency reading of about 5800 Hertz, considerably above the room background noise level of 600 Hertz, and clearly audible to an observer in the room. In comparison, the film sample of this invention had a frequency reading of less than 4000 Hertz, as low as about 2000 Hertz for Sample E-1, which is graphically illustrated in FIG. 4. This graphical representation of FIG. 4 is much closer to that of the background noise of FIG. 1 than to that of FIGS. 2 and 3. Samples E-1 and E-2 are preferred because of their low noise levels, but Samples D-1, D-2, F-1, and F-2 are suitable quiet films made in accordance with the discovery of this invention. The films of the present invention are extremely quiet, can be readily extruded and either heat or dielectrically sealed, and have excellent water vapor and odor barrier properties.

TABLE

| Sample Identification | Material* Composition | Film Gauge** Thickness in Mils | dBA Reading | Frequency** Reading in Hertz Units |
|---|---|---|---|---|
| Background Noise | — | — | 56 | 600 |
| Prior Art Sample I | EVA/PVDC/EVA | 3.0 | 77 | 5,800 |
| Prior Art Sample II | Monolayer PVC | 8.6 | 59 | 750 |
| Prior Art Sample III | PE/EVA/PVDC/EVA/PE | 2.8 | 86 | 11,800 |
| Sample A-1 | 0% CPE, 100% LDPE | 2.6 | 87 | 10,000 |
| Sample A-2 | 0% CPE, 100% LLDPE | 2.8 | 83 | 6,500 |
| Sample B-1 | 17.5% CPE, 80% LDPE | 2.7 | 83 | 5,000 |
| Sample B-2 | 17.5% CPE, 80% LLDPE | 3.0 | 79 | 6,700 |
| Sample C-1 | 37.5% CPE, 60% LDPE | 2.8 | 78 | 5,800 |
| Sample C-2 | 37.5% CPE, 60% LLDPE | 3.0 | 75 | 7,000 |
| Sample D-1 | 57.5% CPE, 40% LDPE | 2.9 | 77 | 3,800 |
| Sample D-2 | 57.5% CPE, 40% LLDPE | 3.1 | 75 | 3,000 |
| Sample E-1 | 67.5% CPE, 30% LDPE | 3.0 | 72 | 2,000 |
| Sample E-2 | 67.5% CPE, 30% LLDPE | 2.8 | 74 | 2,600 |
| Sample F-1 | 77.5% CPE, 20% LDPE | 3.3 | 75 | 3,500 |
| Sample F-2 | 77.5% CPE, 20% LLDPE | 3.3 | 74 | 3,000 |
| Sample G | 97.5% CPE, 0% LDPE or LLDPE | 2.7 | 57 | 800 |

*EVA = Ethylene vinyl acetate copolymer resin such as Elvax brand resin produced by duPont Chemical Company; PVDC = polyvinylidene copolymer such as Saran resin produced by The Dow Chemical Company. Approximate compositions where known. Samples B-1 through G include about 2.5% stabilizers in addition to the CPE blend. Each of the films of Samples B-1 through F-2 are multilayered films having a PVDC core layer, the materials of the skins being designated in the Table.
**Approximate rounded off readings. The gauge is the total thickness for the film structure.

As can be determined from the Table, there are varying degrees of difference in the recorded decibel noise level of the films. The group of films of Prior Art Samples I and III and Samples A-1 through F-2, are all in the 72 to 87 dBA range, which provides some indication of relative quietness. Yet a perceptible difference in quietness is realized by those handling films of a similar The films of Prior Art Sample II and Sample G exhibit quietness levels below that of the films of this invention, both in the dBA and frequency readings. Prior Art Sample II is a polyvinyl chloride monolayer film. This film, while very soft and quiet, has extremely poor water vapor barrier properties, per mil thickness, when compared with other films such as polyethylene or polyvinylidene chloride films. It, therefore, is necessary to make an extremely thick film to have anything approaching adequate vapor barrier using polyvinyl chloride resin. Prior Art Sample II is about three times as thick as the film of this invention. Sample G, while quiet, comprises a heavy concentration of the relatively expensive chlorinated polyethylene resin. This results in higher costs when compared with the other film samples using polyethylene in combination with chlorinated polyethylene. Also, the heavier the concentration of chlorinated polyethylene, the more difficult is the manufacture of the film, as discussed hereinbefore.

The present invention comprehends a superior product capable of providing adequate service when compared to existing products yet maintaining a high degree of quietness so that applications of the product in the form of containers, such as ostomy bags where rustle-free characteristics are of major significance, can be achieved. While certain representative embodiments and details have been shown for purposes of illustrating the invention, it will be apparent to those skilled in the art that various changes and applications can be made therein without departing from the spirit and scope of the invention. For example, a film made from the chlorinated polyethylene blend could be combined with a layer of adhesive resin, such as ethylene acrylic acid or ethylene vinyl acetate, for laminating to substrates such as metal or foam. An adhesive resin such as ethylene vinyl acetate could also be blended with the chlorinated polyethylene resin. The film thickness, coloration or degree of transparency and toughness, can likewise be varied according to the needs of a particular application. The products to be made from the film may not only reside in film pouches for surgical or other medical use, but may find application in many other products where quietness is an important factor, such as in clothing, diapers or in wrappings and other packaging uses.

What is claimed is:

1. A substantially rustle-free thermoplastic product having a film body comprising a multilayer structure, said structure having at least two skin layers and a core layer, a skin layer of said structure comprising a resin blend, a major component of said blend being a chlorinated polyethylene resin, said film when measured against a background noise generating a frequency reading of about 600 Hertz having a noise level generating a frequency reading of less than 4000 Hertz, the composition of the chlorinated polyethylene comprising between about 25 and 50 weight percent chlorine and the balance being substantially an olefinic polymer or copolymer, said polymer or copolymer being low or medium density polyethylene or an ethylene copolymer which comprises ethylene in at least one monoethylenically unsaturated comonomer or a blend of one or more of such polymers or copolymers; the blend of the layer comprising between about 40 and 95 weight percent of the chlorinated polyethylene resin, said core layer being of a different resin than either of said skin layers.

2. The product of claim 1 wherein the composition of the chlorinated polyethylene comprises between about 30 and 42 weight percent chlorine.

3. The product of claim 1 wherein intermediate layers are located between the skin layers and core layer.

4. The product of claim 1 comprising a medical pouch.

5. The product of claim 1 comprising a wrapping film.

6. The product of claim 1 wherein said monoethylenically unsaturated comonomer comprises another lower olefin or a carboxylic acid or an alkyl ester of a monoethylenically unsaturated carboxylic acid.

7. The product of claim 1 wherein said core layer comprises a water vapor and gas barrier resin.

8. The product of claim 7 wherein said barrier resin comprises a vinylidene/vinyl chloride copolymer resin.

9. The product of claim 1 wherein each of the skin layers is comprised of said blend and is about 1 mil or greater in thickness.

10. The product of claim 1 wherein the skin layers are comprised of said blend and comprise more than 80 percent of the total thickness of the material comprising said product.

11. The product of claims 9 or 10 wherein the total film gauge thickness thereof ranges from about 2 mils to about 5 mils.

* * * * *